United States Patent [19]

Callaghan

[11] Patent Number: 4,766,901

[45] Date of Patent: * Aug. 30, 1988

[54] RATE RESPONSIVE PACING SYSTEM USING THE INTEGRATED EVOKED POTENTIAL

[75] Inventor: Frank J. Callaghan, Miami, Fla.

[73] Assignee: Telectronics N.V., Netherlands Antilles

[*] Notice: The portion of the term of this patent subsequent to Aug. 30, 2005 has been disclaimed.

[21] Appl. No.: 810,877

[22] Filed: Dec. 18, 1985

[51] Int. Cl.⁴ .............................................. A61N 1/30
[52] U.S. Cl. ............................................. 128/419 PG
[58] Field of Search .................. 128/419 PG, 704, 707

[56] References Cited

U.S. PATENT DOCUMENTS

| 4,140,132 | 2/1979 | Dahl | 128/419 PG |
| 4,202,339 | 5/1980 | Wirtzfeld et al. | 128/419 PG |
| 4,228,803 | 10/1980 | Rickards | 128/419 PG |
| 4,305,396 | 12/1981 | Wittkampf et al. | 128/419 PG |

FOREIGN PATENT DOCUMENTS 160210 5/1983 German Democratic Rep. ............................. 128/419 PG

OTHER PUBLICATIONS

Fananapazir, et al., "Reliability of the Evoked Response ...," 8 Pace 701-714 (Sep.-Oct. 1985).

Primary Examiner—William E. Kamm
Attorney, Agent, or Firm—George H. Gerstman

[57] ABSTRACT

A rate responsive cardiac pacing system is provided. In the illustrative embodiment, electrical stimulus pulses are applied to the heart ventricle and the evoked potential of the applied electrical stimulus pulses is detected. The detected potential is integrated over time to obtain a depolarization gradient duration. The depolarization gradient duration is compared with a corresponding depolarization gradient duration of at least one previous cardiac cycle. The rate of the electrical stimulus pulses is controlled in response to this comparison.

15 Claims, 8 Drawing Sheets

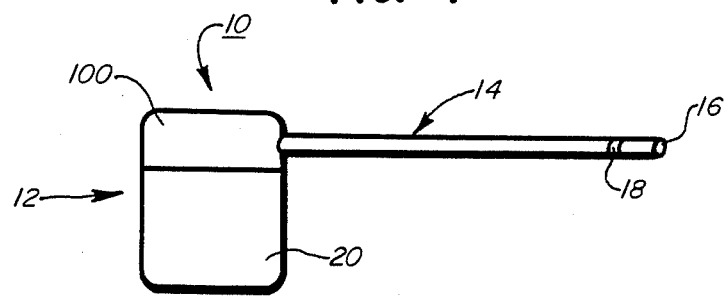
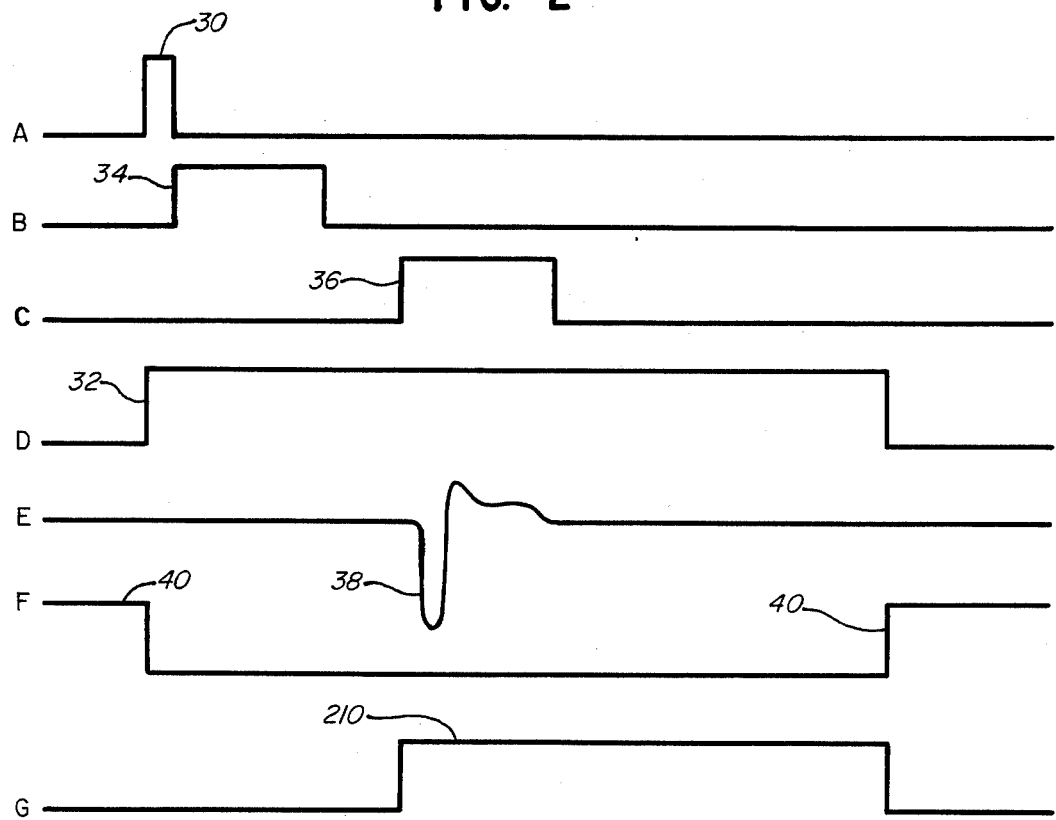

RATE RESPONSIVE PACING SYSTEM USING THE INTEGRATED EVOKED POTENTIAL

CROSS-REFERENCE TO RELATED APPLICATIONS

This application is related to U.S. patent application Ser. Nos. 841,305, 841,478 and 841,517, all filed Mar. 19, 1986, in the name of Frank J. Callaghan.

BACKGROUND OF THE INVENTION

An implantable cardiac pacer can have various pacing modes as well as various output parameters such as rate, output level (current, voltage, pulse duration), sensitivity, refractory period, etc. In some cardiac pacers both the mode, e.g, R-wave inhibited VVI, as well as the various output parameters, are preset during production, whereas in other cardiac pacers either mode or output parameters or both can be altered by external control or programming. Such output parameters and/or pacing mode changes are usually accomplished by the attending physician, usually during an office visit. Therefore, such cardiac pacers may not be responsive to the physiological requirements of the patients. Such requirements fluctuate often during a 24-hour period, certainly more frequently than the interval between patient's visits to the physician. Thus the patient must suffer less than optimum heart pacing.

Increased emphasis is being placed on the use of physiological parameters to control the output parameters, and particularly the rate of stimulation, of implantable cardiac pacers. Such physiological parameters can include activity of the patient (Dahl U.S. Pat. No. 4,140,132), sensed ionic changes (Wirtzfeld U.S. Pat. No. 4,202,339), the patient's threshold, i.e., the level of a stimulus pulse required to evoke a resulting heartbeat when the pulse is delivered to the patient's heart (Wittkampf, et al. U.S. Pat. No. 4,305,396), and the stimulus to repolarization of the T-wave interval (Rickards U.S. Pat. No. 4,228,803). The detection of such changes is utilized either to increase or to decrease the rate of stimulation.

Measurement of physical activity or of the ionic level in the blood does not appear to measure the effectiveness of the pulse emitted from the cardiac pacer initiating myocardial contraction.

While the stimulus repolarization interval on the T-wave can provide information as to stress on the heart, the T-wave is sometimes difficult to detect. This is illustrated in the article by Fananapazir entitled *Reliability of the Evoked Response in Determining the Paced Ventricular Rate and Performance of the QT of Rate Responsive (TX) Pacemaker,* "Pace", vol. 8, pp. 701-714 (September-October, 1985). In this article, it is stated that problems resulted in attempts to provide T-wave sensing in the long term with patients where the system was being used to control heart pacing rates.

Also, the amplitude, as measured from the base line, of the repolarization potential or T-wave tends to be low, thereby posing problems in detection. In addition, within means for detecting the evoked potential of the T-wave, a time period or "window" for sensing of the T-wave must be established and programmed either at manufacture or after implantation. If there is an improper setting of the sensing window, the T-wave may not be sensed. Also, in certain patients, the T-wave may be bimodal; that is, there may be two peaks rather than one. It is possible that the amplitude of the first peak is not sufficient to be detected, and that the second peak may be outside of the sensing window. Alternatively, neither of the peaks of the bimodal T-wave may be of sufficient amplitude to be detected.

In accordance with this invention, a more reliable technique for detecting stress level changes is provided, particularly in a paced heart where it is desirable to provide feedback means so that the rate of pacing of the heart can vary in a manner responsive to heart stress. Improvements of long term reliability and ease of operation are provided by this invention.

SUMMARY OF THE INVENTION

In this invention, a system is provided for applying electrical stimulus pulses to the heart in a manner that is at least partially controlled by stress level changes. To this end, the stress level changes are determined by detecting, in at least one cardiac cycle, the changing voltage of the heart ventricle during depolarization. With this data, the system compares ar least one parameter of the changing voltage with a corresponding parameter of an earlier heartbeat. From this, changes in heartbeat stress levels may be determined.

Electrical stimulus pulses are applied to pace the heart at a rate which is at least partially dependent on the stress level changes so determined, to provide a heart pacing system which is responsive in terms of causing a changed heartbeat rate in response to changes in stress levels of the heart. This, in turn, provides greater patient comfort and greater ability for the patient to lead a normal life, engaging in a greater range of activities calling for different pulse rates.

Numerous parameters of the QRS phase of the cycle may be utilized to determine the heartbeat stress level at any given time, so that changes in the stress level may be determined and, if desired, the pacing rate of a heart adjusted in a manner responsive thereto.

Some of thee parameters may be obtained from an electrocardiographic quantity known as the "Ventricular Gradient". The ventricular gradient is obtained by integrating, over one cardiac cycle, the voltage appearing in a lead which picks up voltage changes from the ventricle. The resulting curve which represents voltage and its changes over time may then be integrated in a standard mathematical manner to obtain the area under the curve within appropriate limits along the curve, typically from the Q-point to the S-point in accordance with this invention. The value of this integral provides a measure of the degree of sympathetic tone of the heart and its stress.

In this invention, a system is provided for detecting in at least one cardiac cycle, the changing voltage of the cardiac ventricle during the QRS phase of the cycle; followed by integrating the changing voltage over time from essentially the Q-point to the S-point to obtain the depolarization gradient. The system then compares the depolarization gradient duration of one cardiac cycle (i.e., heartbeat) with the depolarization gradient duration of at least one previous cardiac cycle. A change in the value of the depolarization gradient duration is an indication of a change in heartbeat stress level. The changes are inversely dependent upon stress in the heart: an increase in the depolarization gradient duration indicates a decrease in heart stress, while a decrease in the depolarization gradient duration indicates an increase in heart stress. Accordingly, when the depolarization gradient duration is sensed to decrease in a pacing system, means are provided to increase the pacing rate to increase the heartbeat and heart output. Conversely, when the depolarization gradient duration increases, it is an indication of less stress and the pacing system slows the heartbeat in response.

Additionally, the system may compare parameters of the QRS complex which indicate heart stress against a target value which has been determined by the medical history of the patient. For example, the system may determine the depolarization gradient duration of at least one heartbeat and then compare the value of the depolarization gradient duration obtained with such target value. If the depolarization gradient duration is less than the target value, the system may increase the rate of electrical stimuli emitted by the heart pacer. If the depolarization gradient duration is greater than the target value, the system may decrease the rate of such electrical stimuli.

As a result of this, a patient having a paced heart is no longer limited to a single electric stimulus rate from visit to visit to the doctor's office to adjust such rate. If he climbs a hill or a flight of stairs, his pacer stimulus rate will increase. When he goes to bed, his stimulus rate will decrease. Thus, patients who are equipped with pacers controlled in accordance with this invention can have a lifestyle which is much closer to normal than in previous pacer systems.

One significant advantage of the ventricular gradient is that its value is independent of the origin of heart stimulation. Hence, naturally conducted beats, paced beats, and ectopic beats can all yield heart stress information by the comparison of ventricular gradients of a present heartbeat with an earlier heartbeat in accordance with this invention.

It should be noted that sensing of the changing voltage of the heart ventricle provides more meaningful data than sensing voltage changes of other portions of the heart, although the system may also sense in accordance with this invention from the atrium.

BRIEF DESCRIPTION OF THE DRAWINGS

FIG. 1 is an elevational view of a cardiac pacing system with a bipolar lead which functions both as a unipolar and a bipolar system at different steps of the operating cycle;

FIG. 2 is a timing diagram of the relationship of the electronic events which take place during a single cardiac cycle;

DETAILED DESCRIPTION OF THE ILLUSTRATIVE EMBODIMENTS

Figure 3:
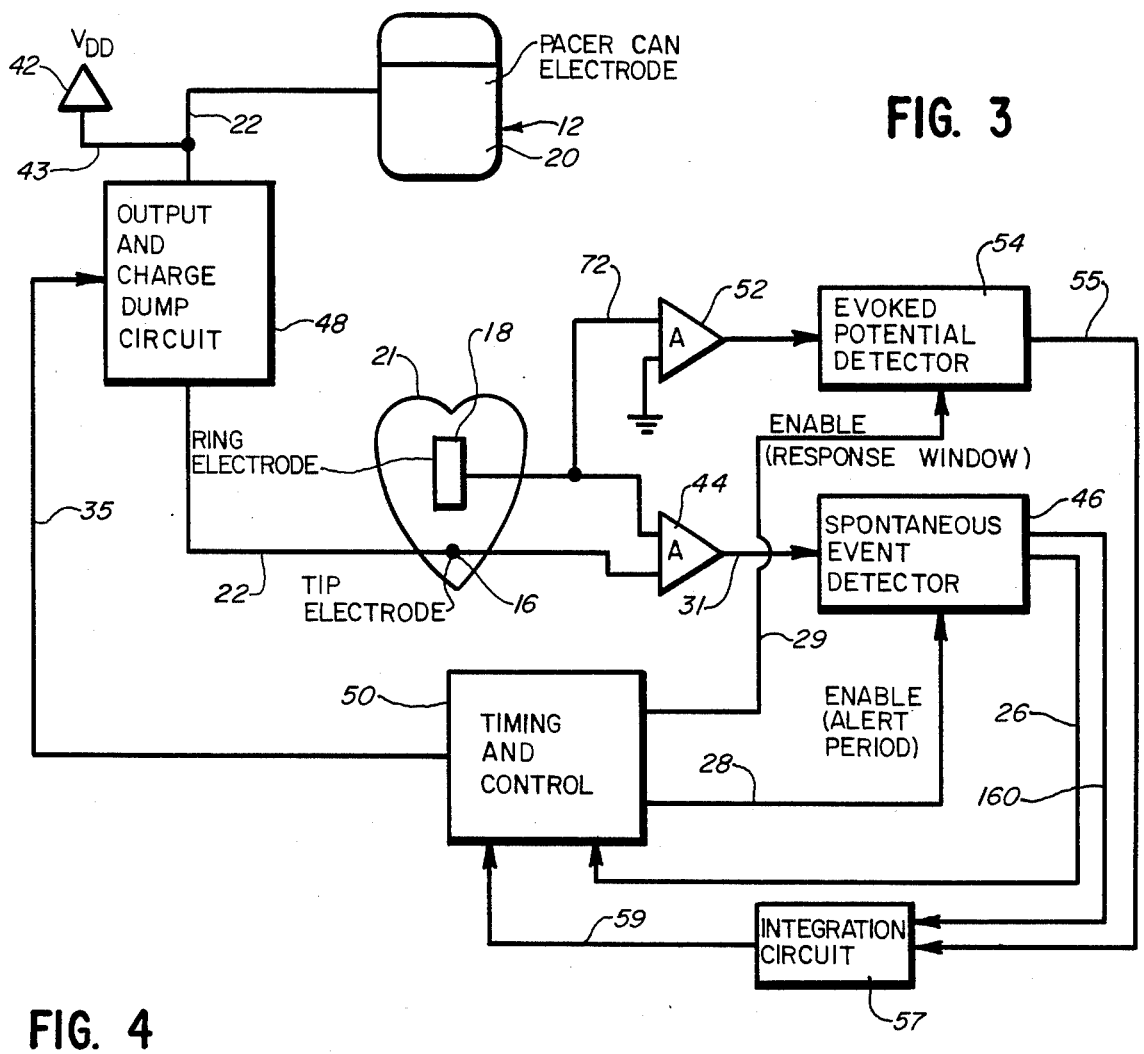
FIG. 3 is a schematic block diagram of a single chamber cardiac pacer with evoked potential monitoring and an integrating circuit.

Referring to the drawings, in FIG. 1 a single chamber cardiac pacing system 10 includes pulse generator 12, which may be of generally conventional electronics except as otherwise described herein. Pervenous bipolar lead 14 is also provided and may be of conventional bipolar pervenous or epicardial design.

First electrode 16 may be a porous, platinum-iridium, hemispherically shaped electrode on the distal end of lead 14, communicating with a metal conductor inside of the lead. Ring electrode 18 serves as a second electrode, being capable of electrical isolation by means of the circuitry and pulse generator 12 from first electrode 16, and being typically spaced at least 0.5 cm. from first electrode 16. Second, ring-shaped electrode 18 may also be made of the same alloy and may communicate with its own circuit wire within lead 14 and may or may not be porous-coated.

The circuitry of pulse generator 12 may be sealed in a hermetic container, for example, titanium can 20, as shown. When the pacer can 20 is treated as an independent electrode, the single chamber cardiac pacing system 10 carries three electrodes: can 20, first electrode 16 and second electrode 18. The operation of the pacing system as described applies to both the atrial and ventricular leads of a dual chamber cardiac pacer or an atrial standby pacer. However, for purposes of simplicity of disclosure, the details of operation will be disclosed for only a ventricular pacer. For additional disclosure concerning the detection of cardiac evoked potentials, reference is made to Herscovici U.S. Pat. No. 4,543,956 and to the evoked potential detection and pacing system disclosed is copending U.S. application Ser. No. 807,547, filed Dec. 11, 1985, in the names of Frank J. Callaghan and Edward A. Schroeppel, and entitled "Detection Of Cardiac Evoked Potentials."

Cardiac pacing system 10 may be external or surgically installed into the patient, and may operate to pace the patient's heart as follows:

A pacing cycle begins when an electrical stimulus is emitted from first electrode 16 to stimulate muscular contraction of at least a portion of the heart. The stimulus is of a magnitude and duration which is not harmful to the heart and which is well-known to those skilled in the art to evoke a contraction response from the heart muscle. The pulse of electric stimulus 30 is graphed in FIG. 2 at channel A, having a typical duration of 0.1 to 2 milliseconds.

Referring to the circuit of FIG. 3, pacer can 20 is shown serving as a reference electrode for electrodes 16, 18, carried at the heart 21 which is shown in schematic manner. Stimulus 30 is transmitted via conductor 22 to be emitted from tip electrode 16. The naturally occurring cardiac electrical activity is amplified by amplifier 44 and transmitted via line 31 to a spontaneous event detector 46 to begin a timing process. The signal proceeds via conductor 26 into timing and control circuitry module 50 which, in turn, has feedback and control wires 28, 29 connected, respectively, to detector 46 and to evoked response detector 54. Likewise, an output from timing and control circuit 50 is connected via line 35 to output and charge dump circuit 48.

Figure 4:
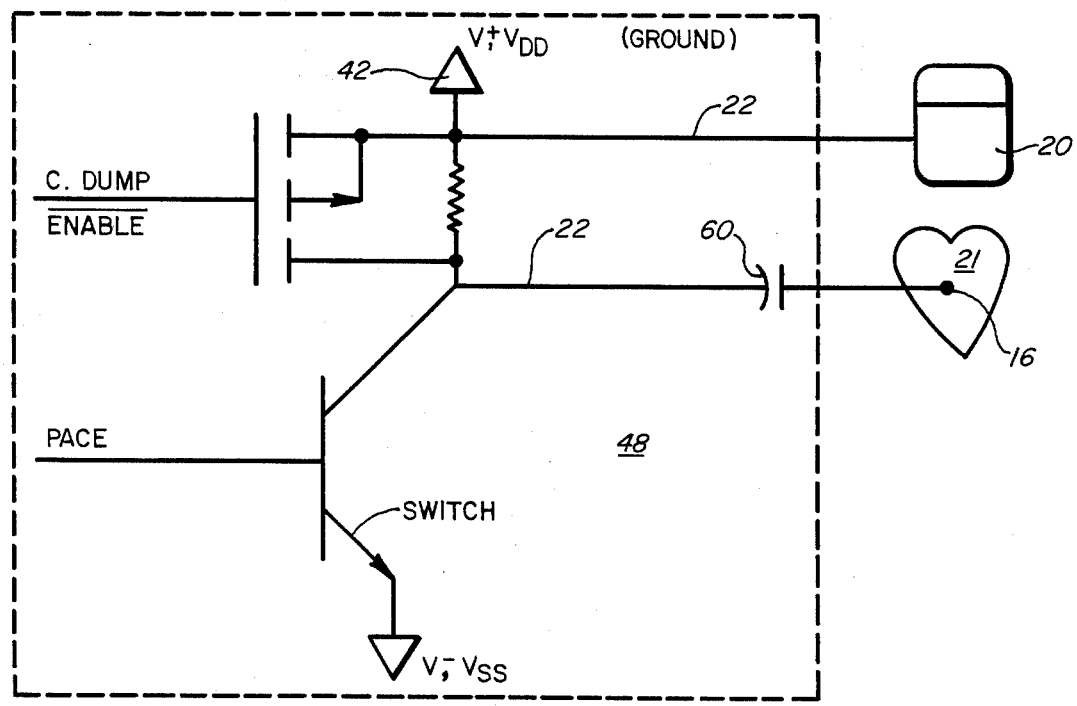
FIG. 4 is a schematic block diagram of the charge dump circuit used herein.

Immediately following the emission of pulse 30 from electrode 16, charge dump circuit 48 is activated, with the charge dump pulse 34 being illustrated on channel B of FIG. 2, the duration of the charge dump being about 5 to 15 milliseconds. The charge dump may be provided using a conventional charge dump circuit 48 such as illustrated in FIG. 4. During the charge dump period, the electrical charge on output coupling capacitor 60 (FIG. 4) and first electrode 16 are discharged through the heart 21. Thus the post-stimulus polarization potential of electrode 16 is quickly diminished.

Evoked response detector 54 is then activated by timing and control circuit 50 through conductor 29. A window of time 36 is opened as illustrated in channel C of FIG. 2, its duration being typically 10 to 50 milliseconds. It is only during this time that evoked response detector 54 is activated to detect an evoked electrical response from the heart and to indicate a contractile response to the physiological pulse of electric potential 30.

The stimulus from electrode 16 can be seen to be in the unipolar mode. Likewise, detection of the evoked response is unipolar, being detected by electrode 18, which communicates through conductor 72 to amplifier 52, which sends the amplified signal to detector 54. Detector 54 transmits the detected signal via line 55 to integration circuit 57. The integrated signal, which is discussed in detail below, is transmitted to timing and control circuit 50 via line 59.

It is noted that the window of time 36 on channel C of FIG. 2 is positioned in a block of time 32 (channel D of FIG. 2) which generally represents a refractory period in which first electrode 16 may not be used to sense any electrical activity. However, the evoked response can be detected during a refractory period 32.

Channel E in FIG. 2 shows the evoked cardiac electrical activity 38 within evoked response detection period 36, and which is detected by second electrode 18. The evoked heartbeat response 38 is detected by second electrode 18 in the unipolar mode. The detected evoked response which is fed via line 55 to integration circuit 57 and via line 59 to timing and control circuit 50 may serve to set the timer to zero for timing the next physiological pulse to be emitted from first electrode 16.

However, there is a need to determine that natural heartbeats will not show up at unexpected times, to avoid the result where the pacing system disrupts and interferes with the natural heartbeat. To this end, beginning essentially at the end of refractory period 32, during which spontaneous event detector 46 is disabled from sensing electric pulses, an alert period 40 (channel F; FIG. 2) is provided to monitor a naturally occurring cardiac electrical activity until such time as the next pulse 30 is sent out through first electrode 16. Alert circuitry 46 may be activated and shut down by timing and control circuit 50 via line 28. When the alert phase 40 is in operation, both electrodes 16 and 18 are operating together in a bipolar mode, with both electrodes communicating with amplifier 44, which in turn is connected to spontaneous event detector 46.

In the event of a spontaneous heartbeat, a signal may be sent from spontaneous event detector 46 via line 26 to timing and control circuit 50, to cause the electronics to recycle from any time in the cycle to the beginning of the cycle, without generation of an electric pulse 30 from first electrode 16. Every time natural cardiac electrical activity takes place during alert period 40, no electric pulse 30 will be generated.

In the event, however, that detector 46 does not detect natural cardiac electrical activity during the alert period, timing and control circuit 50 will cause another electric pulse to be generated via electrode 16.

Figure 5:
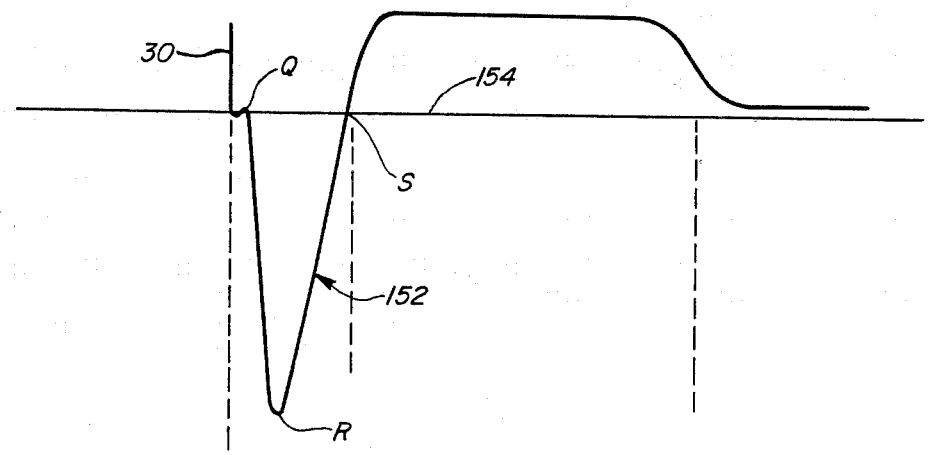
FIG. 5 is a diagram of the evoked potential over time sensed by a pacer and lead of FIG. 1 positioned at a heart ventricle.

Referring to FIG. 5, a typical cardiograph tracing of the changing potential in the ventricle of a heart is shown throughout most of a single cardiac cycle with respect to a reference base line of a predetermined voltage, typically zero volts. For purposes of this invention, the Q-point represents the beginning of the R-wave 152 where the voltage trace crosses or is closest to base line 154, prior to forming R-wave 152. The R-point is the peak of R-wave 152, irrespective of whether the trace is shown in its form of FIG. 5 or in inverted form, which is possible with other recording systems. The S-point is where the trace crosses base line 154.

Figure 6:
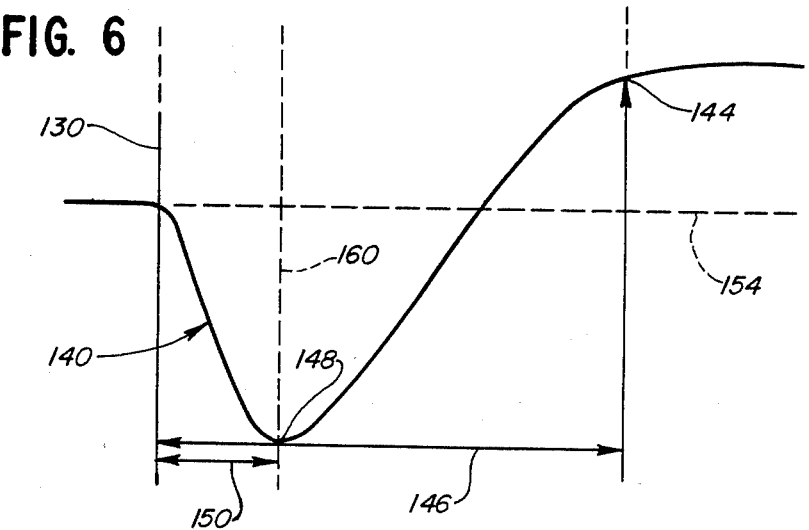
FIG. 6 is a diagram showing the integrated value of the evoked potential of FIG. 5, in horizontal time synchronization with FIG. 5.

In operation, as illustrated in FIG. 3, the evoked potential is detected on ring electrode 18. The signal is transmitted via heart amplifier 52 and detector 54 to integration circuit 57 via line 55. The integrated signal 140 is known as the ventricular gradient, and is illustrated in FIG. 6. Referring to FIG. 6, there are two major time periods of interest. The first is from the time of the stimulus 30 to the peak 148 of the ventricular gradient 140. This time may be referred to as the depolarization gradient duration 150. The second is the time from the stimulus 30 by electrode 16 to the peak 144 of the integrated repolarization wave. This time period may be referred to as the repolarization gradient duration 146.

During periods of heart stress, R wave 152 shortens in duration. Therefore, the depolarization gradient duration 150 will similarly decrease in duration. The depolarization duration 150 lends itself to detection and analysis. The occurrence of bimodal R waves will not negatively impact upon the value of the depolarization gradient duration 150 as a stress measuring tool.

The depolarization gradient duration 150 is calculated and compared to the depolarization gradient duration of a response detected prior to this one. The average time of three (or some predetermined number of) depolarization gradient durations may be used. In this case, each response should change in the same direction. If the depolarization gradient duration 150 is equal to the previous value, there is no change in the heart pacing stimulus rate. The escape interval remains the same. If the depolarization gradient duration 150 is shorter than the prior value, or there has been a change in the same direction of the three (or some other predetermined number) depolarization gradient durations, a determination is made as to whether or not the stimulus rate is at its programmed maximum rate. If it is at its maximum rate, the depolarization gradient duration is stored and the stimulus rate is not increased. However, if the stimulus rate is less than the programmed maximum rate, the rate is incremented by some predetermined value, and the depolarization gradient duration is stored for reference at the next subsequent integrated evoked heart response. Should the depolarization gradient duration increase, indicating a reduction in stress, the determination is made as to whether or not the rate of stimulation is at its minimum programmed rate. If it is at the programmed minimum rate, the depolarization gradient duration is stored with no decrease in rate. If it is not at its minimum programmed rate, the rate of the stimulation is decreased by some predetermined value, and the depolarization gradient duration is stored for future reference.

Additionally, spontaneous electrical events such as those conducted from the atrium to the ventricle via the cardiac conduction pathway or those arising within the ventricle itself, and premature ventricular contractions are detected bipolarly by the ring and tip. These signals are amplified by the amplifier 44 and detected in the spontaneous event detector 46. The timing and control circuit 50 acts upon these events to reset the escape interval. Further, these spontaneous electrical events may be integrated if desired, and the duration 150 of the depolarization gradient may be determined. Rate changes or escape interval changes may be implemented based on the depolarization gradient duration of the spontaneous electrical events in the same manner that they are implemented based on the depolarization gradient duration of the evoked potentials. To this end, the integration circuit 57 of FIG. 3 is shown as receiving the signal from the spontaneous event detector 46 via line 160.

Figure 7:
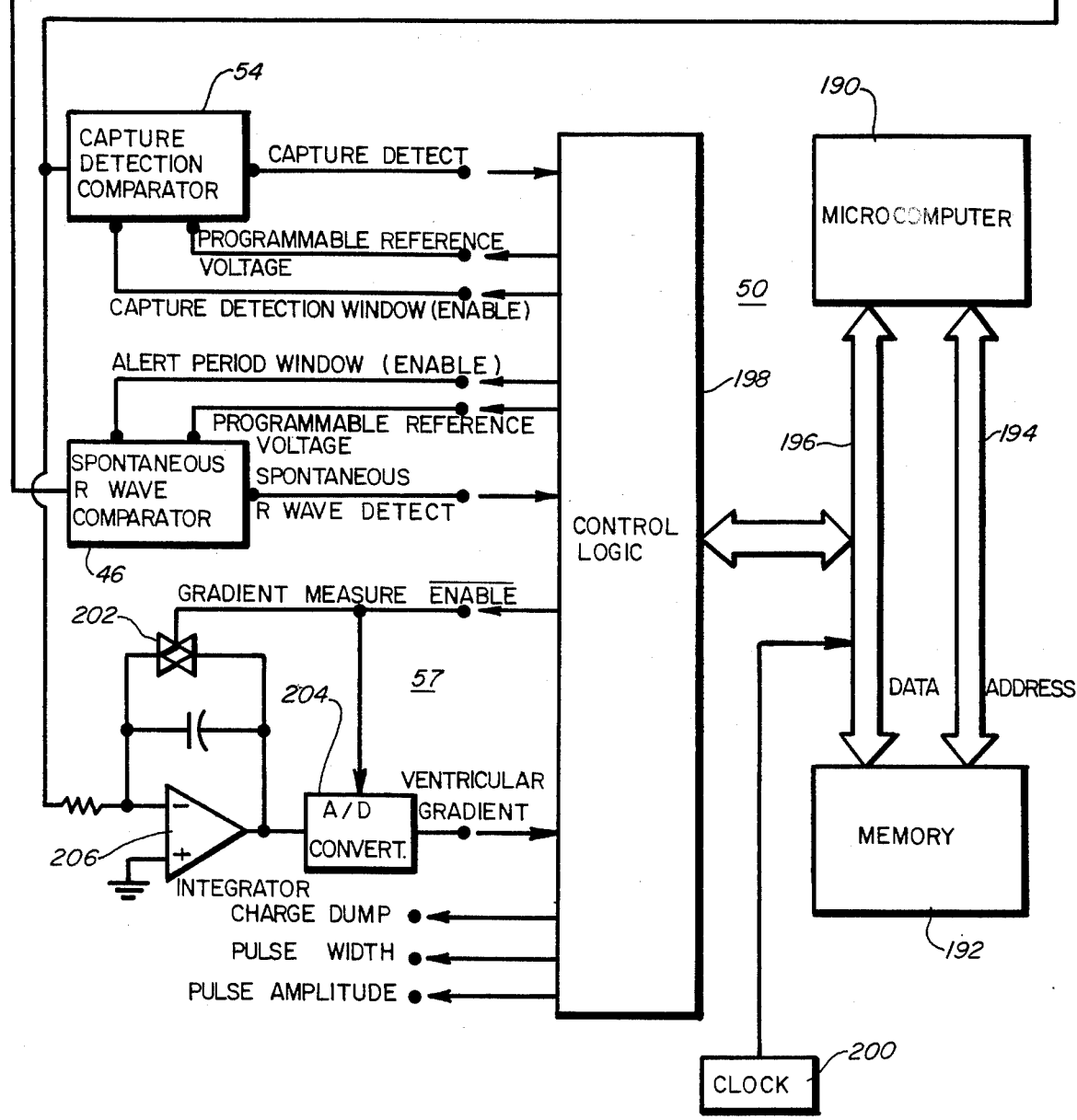
FIG. 7 is a schematic diagram of a pacer system constructed in accordance with the present invention.

A relatively detailed schematic diagram of the pacer electronics is presented as FIG. 7. Referring to FIG. 7, it is seen that the same reference numerals are used for the same components of FIG. 3. Timing and control circuit 50 comprises a microcomputer 190 which addresses a memory 192 via address bus 194. Data bus 196 is coupled between microcomputer 190 and memory 192, and conventional control logic 198 is coupled to data bus 196. A crystal controlled clock 200 is used for providing appropriate clock pulses for the system. The functions of the control logic inputs and outputs are designated.

Control logic circuit 198 provides a gradient measure enable signal to electronic switch 202 and to analog to digital converter 204 which is at the output of an integrating amplifier 206. It can be seen that the output of the amplified potential sensed at ring 18 is applied to the negative input of integrating amplifier 206 which, when enabled, provides an amplified analog output that is converted to digital data by means of analog to digital converter 204. The digital data contains the ventricular gradient information, which is provided to the control logic circuit 198 whereby appropriate timing of the stimulation pulses is achieved in response thereto.

The gradient measure enable signal 210 is illustrated in channel G on FIG. 2. It commences at the same time that the capture detection window 36 commences and the gradient measure enable signal 210 continues for several hundred milliseconds.

Figure 8A:
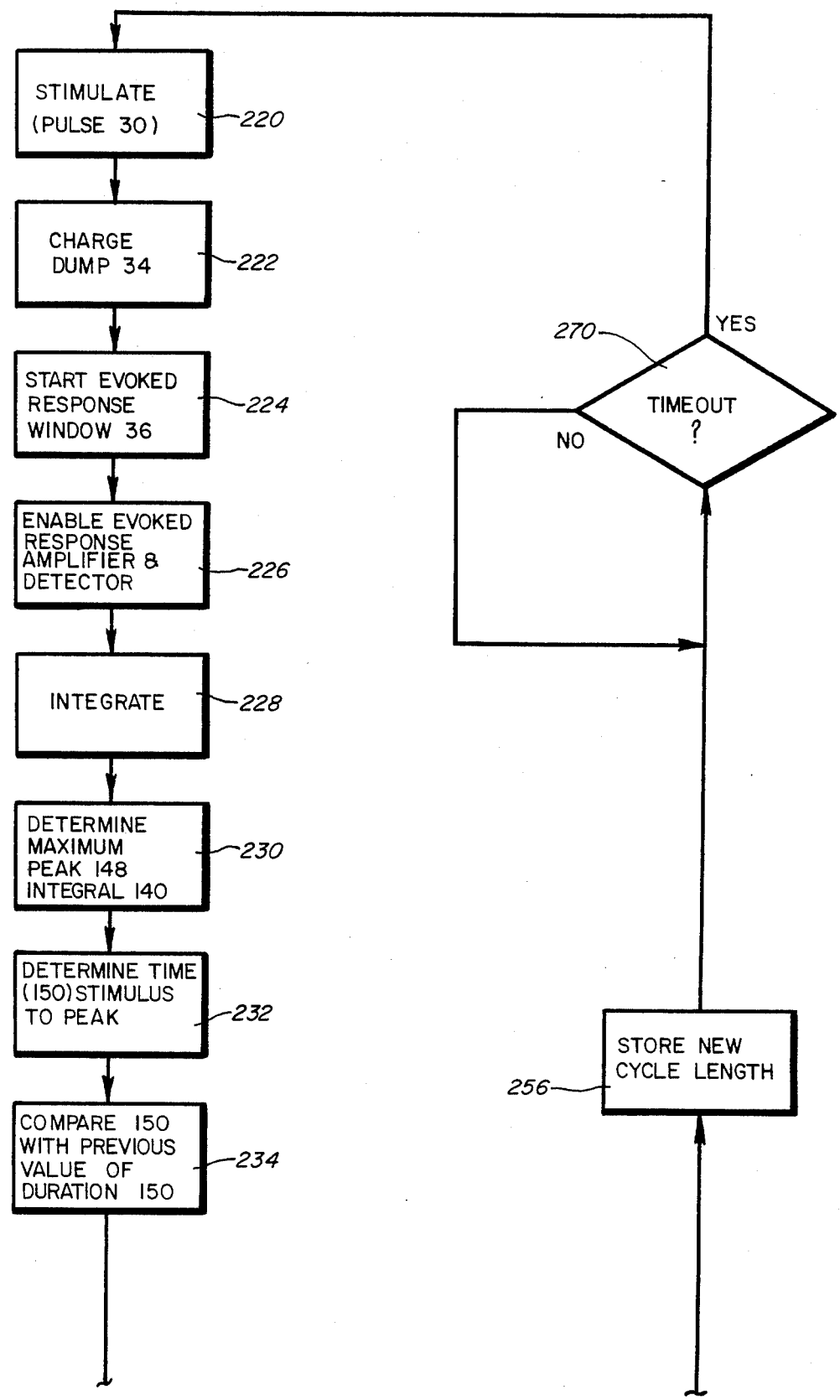
FIGS. 8a and 8b, when connected together, comprise a flow chart depicting the operation of the diagram of FIG. 7.
Figure 8B:
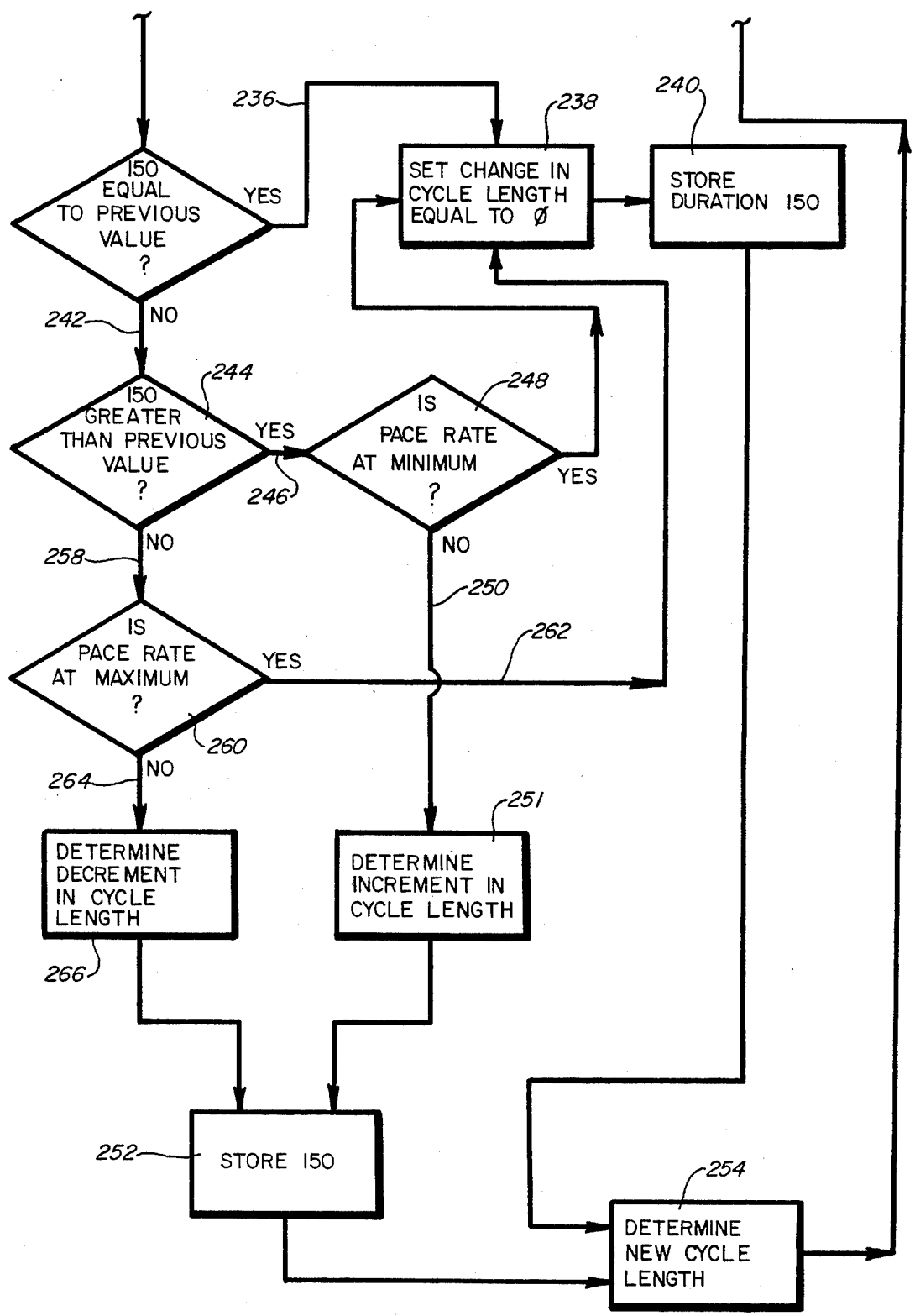

A flow chart illustrating the operation of the circuit of FIG. 7 is presented as FIGS. 8a-8b. Referring to FIGS. 8a-8b, the cycle starts with a stimulation pulse 30 being emitted (220). After charge dump 34 (222), the evoked response window 36 commences (224) and the evoked response amplifier and detector is enabled (226). The gradient measure enable signal 210 also commences and the evoked response is integrated (228) and the maximum peak 148 of the integral 140 is determined (230). The time from the stimulus 30 to peak 148, which time is the depolarization gradient duration 150, is then determined (232). The depolarization gradient duration 150 is then compared (234) with the previous value of the depolarization gradient 150. If they are equal (236), the pacing rate, i.e., cycle length, is not changed (238) and the duration 150 is stored (240). If they are not equal (242), a determination is made (244) whether the present duration 150 is greater than the previous duration 150. If it is greater (246), a determination (248) is made whether the pacing rate is at its minimum. If it is at its minimum, there will be no further change in pacing rate (238) and the duration 150 will be stored (240). If it is not at its minimum (250), a determination (251) will be made with respect to decreasing the present pacing rate, and the duration 150 is stored (252). A new decreased pacing rate (i.e., increased cycle length) is determined (254) and stored (256).

On the other hand, if it is determined that the present duration 150 is not equal to its previous value (242) and is also not greater than its previous value (258), this indicates that present duration 150 is less than previous duration 150. A determination is then made whether the pacing rate is at its maximum (260) and if it is at its maximum (262), the cycle length is not changed (238) and the duration 150 is stored (240). If the pacing rate is not at its maximum (264), a determination (266) is made with respect to the decrement in the cycle length (i.e., the increase in pacing rate) and the duration 150 is stored (252). A determination (254) is then made with respect to the new increased pacing rate (i.e., decreased cycle length) and this information is stored.

When the rate timer times out (270), a new stimulation pulse 30 is issued (220) and the cycle will again commence.

Figure 9A:
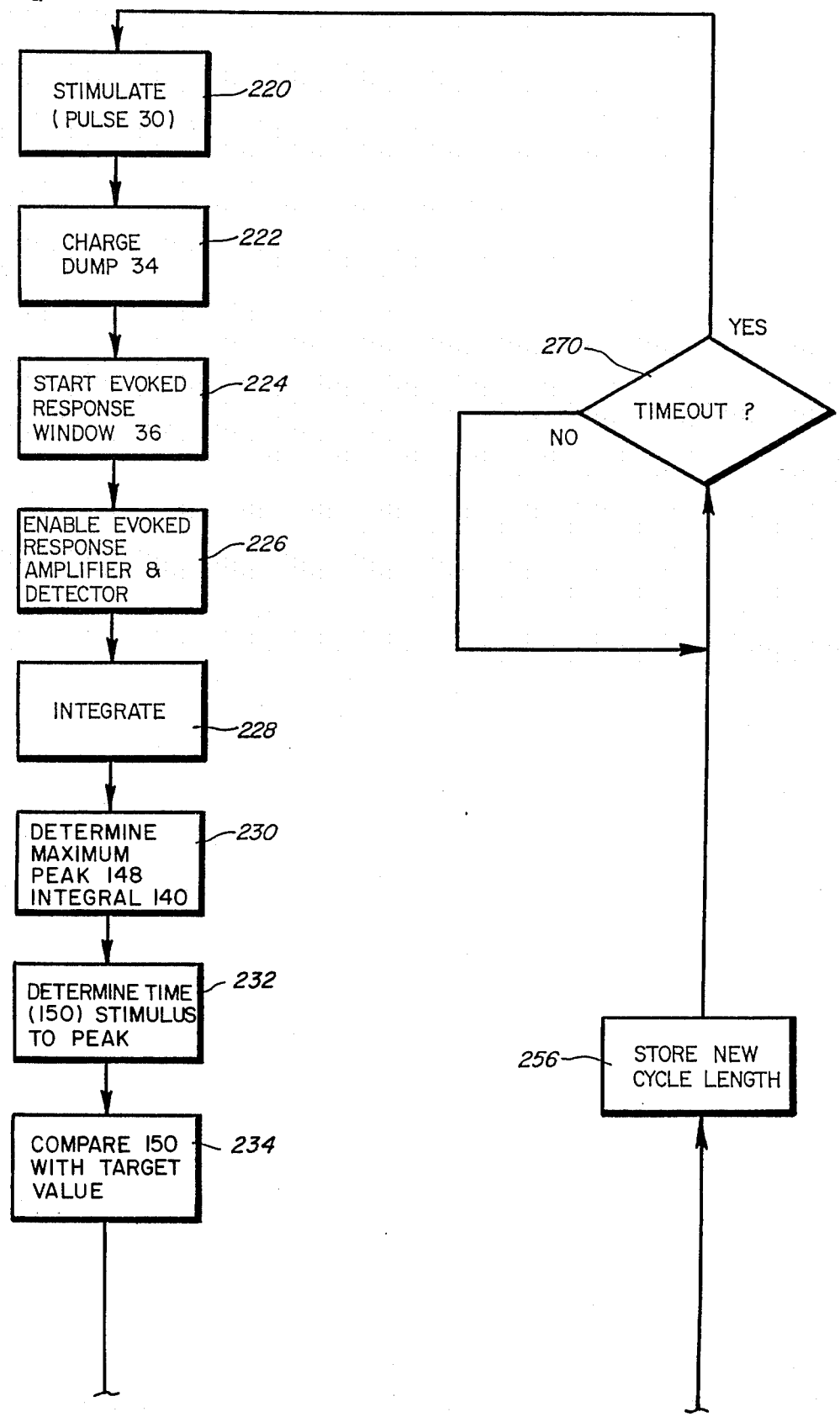
FIGS. 9a and 9b, when connected together, comprise a flow chart depicting the operation of another embodiment of the invention.
Figure 9B:
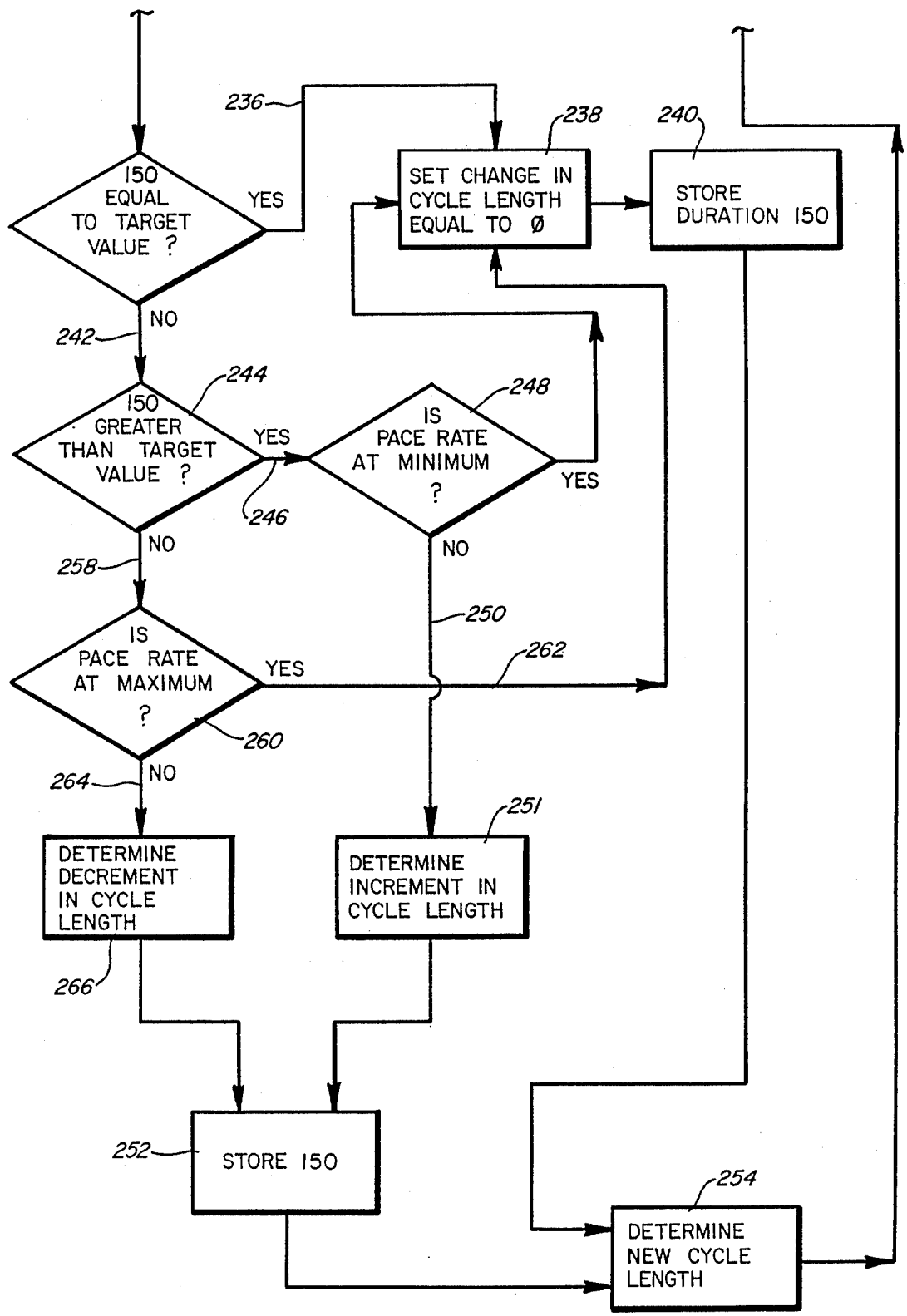

FIGS. 9a-9b illustrate the operation of the circuit of FIG. 7 when the duration 150 is compared against a target value instead of being compared against the previous value of duration 150. Referring to FIGS. 9a and 9b, it is seen that the operation of the circuit is identical to the operation of the FIGS. 8a-8b circuit except that instead of comparing duration 150 with the previous value of duration 150, duration 150 is compared against the target value which has been determined by the medical history of the patient.

Although an illustrative embodiment of the invention has been shown and described, it is to be understood that various modifications and substitutions may be made by those skilled in the art without departing from the novel spirit and scope of the present invention.

What is claimed is:

1. A cardiac pacing method which comprises the steps of:
    applying electrical stimulus pulses to the heart;
    detecting the evoked potential of said applied electrical stimulus pulses;
    integrating said detected potential over time to obtain a selected parameter;
    storing said selected parameter;
    comparing said selected parameter with a corresponding selected parameter of at least one previous cardiac cycle that has been stored; and
    controlling the rate of said electrical stimulus pulses in response to said comparison.

2. A method as described in claim 1, in which the rate controlling step includes the steps of not changing the pacing rate if the compared selected parameters are equal, varying the pacing rate in one direction if the selected parameter is less than the prior value, and varying the pacing rate in the opposite direction if the selected parameter is greater than the prior value.

3. A method as described in claim 1, wherein said selected parameter comprises the depolarization gradient duration.

4. A method as described in claim 3, including the steps of sensing the occurrence of the electrical stimulus pulse and the occurrence of the peak of the integrated evoked potential to obtain the depolarization gradient duration.

5. A method as described in claim 4, in which the controlling step includes the steps of not changing the pacing rate if the compared depolarization gradient durations are equal, increasing the pacing rate if the depolarization gradient duration is less than the prior value, and decreasing the pacing rate if the depolarization gradient duration is greater than the prior value.

6. A method as described in claim 5, in which the rate controlling step comprises the following steps: if the depolarization gradient duration is less than the prior value, then determining if the pacing rate is at a predetermined maximum; and if the pacing rate is at a predetermined maximum, then not changing the pacing rate rate, but if the pacing rate is less than said predetermined maximum then increasing the pacing rate; and if the depolarization gradient duration is greater than the prior value, then determining whether the pacing rate is at a predetermined minimum value; and if the pacing rate is at a predetermined minimum value, then not changing the pacing rate, but if the pacing rate is greater than said predetermined minimum then decreasing the pacing rate.

7. A cardiac pacing method which comprises the steps of:
   applying electrical stimulus pulses to the heart ventricle;
   detecting the evoked potential of said applied electrical stimulus pulses;
   integrating said detected potential over time to obtain a selected parameter;
   comparing said selected parameter with a target value; and
   controlling the rate of said electrical stimulus pulses in response to said comparison.

8. A method as described in claim 7, wherein said selected parameter comprises the depolarization gradient duration.

9. A method as described in claim 8, including the steps of sensing the occurrence of the electrical stimulus pulse and the occurrence of the peak of the integrated evoked potential to obtain the depolarization gradient duration.

10. Cardiac pacing apparatus which comprises:
    means for applying electrical stimulus pulses to the heart;
    means for detecting the evoked potential of said applied electrical stimulus pulses;
    means for integrating said detected potential over time to obtain a selected parameter;
    means for storing said selected parameter;
    means for comparing said selected parameter with a corresponding selected parameter of at least one previous cardiac cycle that has been stored; and
    means for controlling the rate of said electrical stimulus pulses in response to said comparison.

11. Apparatus as described in claim 10, in which said controlling means includes means for maintaining the pacing rate constant if the compared selected parameters are equal, means for varying the pacing rate in one direction if the selected parameter is less than the prior value, and means for varying the pacing rate in the opposite direction if the selected parameter is greater than the prior value.

12. Apparatus as described in claim 11, including means for determining if the pacing rate is at a predetermined minimum, means for determining if the pacing rate is at a predetermined maximum, said controlling means being operable to maintain the pacing rate if the pacing rate is at one of a predetermined maximum and a predetermined minimum.

13. Cardiac pacing apparatus as described in claim 10, wherein said selected parameter comprises the depolarization gradient duration.

14. Cardiac pacing apparatus as described in claim 13, including means for sensing the occurrence of the electrical stimulus pulse and the occurrence of the peak of the integrated evoked potential, to obtain the depolarization gradient duration.

15. Apparatus as described in claim 14, in which said controlling means includes means for maintaining the pacing rate constant if the compared depolarization gradient durations are equal, means for increasing the pacing rate if the depolarization gradient duration is less than the prior value, and means for decreasing the pacing rate if the depolarization gradient duration is greater than the prior value.

* * * * *